United States Patent
Goh

(10) Patent No.: US 9,814,925 B2
(45) Date of Patent: Nov. 14, 2017

(54) EXERCISE MAT, ENTERTAINMENT DEVICE AND METHOD OF INTERACTION BETWEEN THEM

(71) Applicant: Sony Interactive Entertainment Inc., Tokyo (JP)

(72) Inventor: Yee Woon Goh, London (GB)

(73) Assignee: Sony Interactive Entertainment Inc. (JP)

( * ) Notice: Subject to any disclaimer, the term of this patent is extended or adjusted under 35 U.S.C. 154(b) by 52 days.

(21) Appl. No.: 14/963,737

(22) Filed: Dec. 9, 2015

(65) Prior Publication Data

US 2016/0166876 A1    Jun. 16, 2016

(30) Foreign Application Priority Data

Dec. 11, 2014    (GB) .................................. 1422014.9

(51) Int. Cl.
  *A63B 24/00*    (2006.01)
  *A63B 21/00*    (2006.01)
  *G06F 19/00*    (2011.01)

(52) U.S. Cl.
  CPC ...... *A63B 21/4037* (2015.10); *A63B 24/0062* (2013.01); *A63B 24/0075* (2013.01);
  (Continued)

(58) Field of Classification Search
  CPC ....... A63B 24/00; A63B 24/0062; A63B 6/00; A63B 24/075; A63B 2220/56;
  (Continued)

(56) References Cited

U.S. PATENT DOCUMENTS 5,839,976 A    11/1998  Darr
7,645,211 B1    1/2010  Thomeczek et al.
(Continued)

FOREIGN PATENT DOCUMENTS

CN    201171898    12/2008
CN    203329344 U    12/2013
(Continued)

OTHER PUBLICATIONS

Lunar Tera, Jun. 5, 2014, lunar.com, [online], Available from: http://www.lunar.com/introducing-tera/ [Accessed Jun. 3, 2015].
(Continued)

*Primary Examiner* — Glenn Richman
(74) *Attorney, Agent, or Firm* — Lerner, David, Littenberg, Krumholz & Mentlik, LLP

(57) ABSTRACT

An exercise system includes a flexible exercise mat having a flexible body and a plurality of lights incorporated into the flexible body and visible in use on a surface of the flexible body. The system also includes an entertainment device having an input to receive a captured video image of a scene with the flexible exercise mat having the lights visible thereon. An image processor of the entertainment device detects positions of the lights within the image, and a processing device calculates a configuration of shape adopted by the exercise mat based upon the detected positions of the lights. In one mode, the lights are arranged to indicate a configuration of shape adopted by the exercise mat due to a surface upon which it has been placed. The entertainment device modifies a behaviour of an application in response to the configuration of shape of the exercise mat.

12 Claims, 4 Drawing Sheets

(52) U.S. Cl.
CPC ...... *G06F 19/3481* (2013.01); *A63B 2207/02* (2013.01); *A63B 2220/56* (2013.01); *A63B 2220/806* (2013.01); *A63B 2220/833* (2013.01); *A63B 2225/20* (2013.01)

(58) Field of Classification Search
CPC ........ A63B 2220/806; A63B 2220/833; A63B 2225/20; A63B 2207/02; A63B 21/4037; A63F 1/02; A63F 13/35; A63F 13/42; G06F 19/3481
See application file for complete search history.

(56) References Cited

U.S. PATENT DOCUMENTS

| | | | |
|---|---|---|---|
| 8,066,195 B2* | 11/2011 | Takano | A63F 1/02 235/454 |
| 8,605,990 B2* | 12/2013 | Izumi | A63B 6/00 345/419 |
| 9,095,775 B2* | 8/2015 | Collard | G06F 3/011 |
| 9,595,108 B2* | 3/2017 | Horovitz | A63F 13/65 |
| 2006/0252541 A1 | 11/2006 | Zalewski et al. | |
| 2010/0076347 A1 | 3/2010 | McGrath et al. | |
| 2010/0178982 A1 | 7/2010 | Ehrman | |
| 2010/0216598 A1 | 8/2010 | Nicolas et al. | |
| 2010/0285882 A1 | 11/2010 | Hsu | |
| 2012/0015334 A1 | 1/2012 | Hamilton | |
| 2013/0260886 A1 | 10/2013 | Smith | |
| 2014/0071103 A1 | 3/2014 | Yang et al. | |
| 2014/0078312 A1 | 3/2014 | Zalewski et al. | |

FOREIGN PATENT DOCUMENTS

| | | |
|---|---|---|
| GB | 2467951 A | 8/2010 |
| KR | 20110125556 A | 11/2011 |
| WO | 2010019277 A3 | 2/2010 |
| WO | 2010133988 A1 | 11/2010 |

OTHER PUBLICATIONS

Combined Search and Examination Report for Application No. GB1422014.9 dated Jun. 8, 2015.
Extended European Search Report for Application No. 15188171.1, dated Apr. 19, 2016.
Examination and Search Report for Application No. GB1422014.9 dated Dec. 22, 2015.

* cited by examiner

EXERCISE MAT, ENTERTAINMENT DEVICE AND METHOD OF INTERACTION BETWEEN THEM

CROSS REFERENCE TO RELATED APPLICATIONS

The present application claims the benefit of and priority to GB Application No. 1422014.9, filed Dec. 11, 2014, the entire disclosure of which is incorporated by reference herein.

BACKGROUND OF THE INVENTION

Field of the invention

The present invention relates to an exercise mat, entertainment device and method of interaction between them.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There have been several attempts to integrate fitness equipment into video games. One example is the Nintendo® balance board, which is a rigid device resembling a set of electronic scales and comprising an array of four pressure pads that enable a connected entertainment device to determine a user's centre of gravity above the board. Another example is the Luna Tera® yoga mat, which comprises lights and pressure sensors, and integrates with an app to guide a user through an exercise regime and record their performance.

However, these mats still provide only a limited number of options for a user and the entertainment device that is guiding the user's activities.

The present invention seeks to alleviate or mitigate this problem.

SUMMARY OF THE INVENTION

In a first aspect, an exercise system is provided in accordance with claim 1.

In another aspect, a method of interaction between an entertainment device and exercise mat is provided in accordance with claim 13.

Further respective aspects and features of the invention are defined in the appended claims.

It is to be understood that both the foregoing general description of the invention and the following detailed description are exemplary, but are not restrictive, of the invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
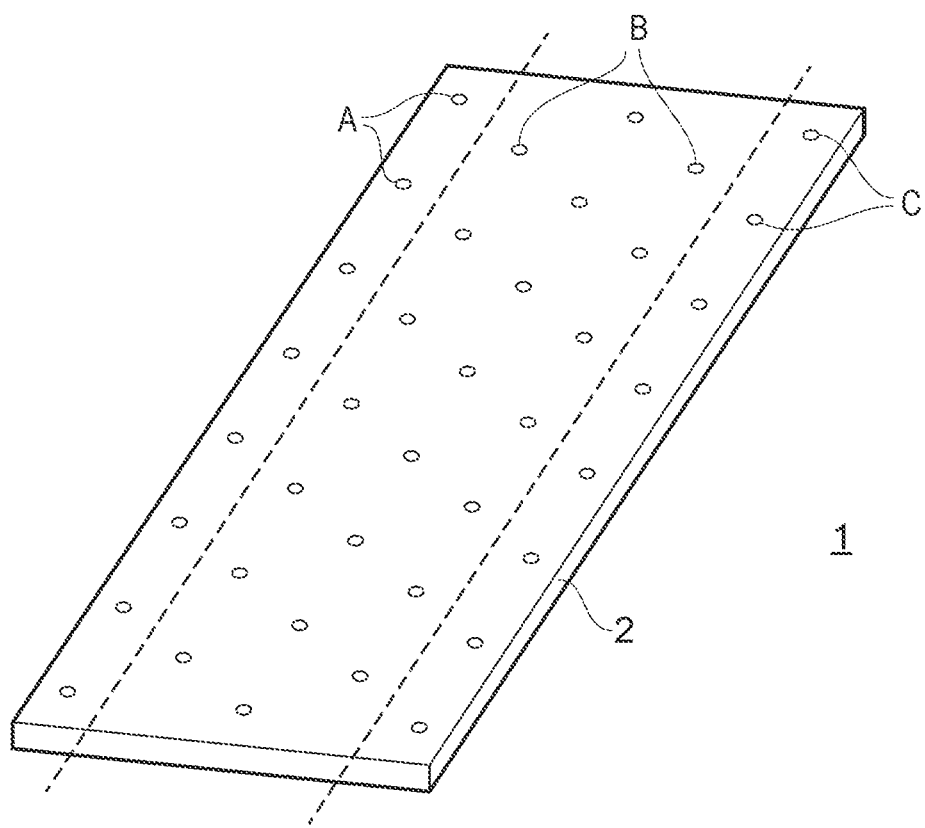
FIG. 1 is a schematic diagram of an exercise mat in accordance with an embodiment of the present invention.

Referring now to the drawings, wherein like reference numerals designate identical or corresponding parts throughout the several views, an exercise mat, entertainment device and method of interaction between them are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

Referring now to FIG. 1, an exercise mat (1) comprises a flexible body (2), made for example from neoprene, latex or PVC, or any flexible and substantially non-absorbent material. It is preferable to not use of absorbent natural fibres such as cotton, wool or jute as these can absorb sweat easily, which is then difficult to wash out due to the presence of electronics within the mat. However, if such natural fibres are used, it is preferable but not essential to include a waterproof top layer or a replaceable sacrificial top layer. The bottom surface is preferably non-slip, and so may comprise a non-slip layer where the flexible body of the mat is not made from a non-slip material. Preferably the exercise mat is sufficiently flexible to be rolled up for storage.

The above mentioned electronics comprise a plurality of lights (A, B, C) incorporated into the flexible body. In an embodiment of the present invention, the lights are LEDs embedded within recesses in the upper surface of the exercise mat. The recesses may be open to the surface so that the LEDs are at least in part clear of the flexible body, or the recesses may be closed to the surface so that the LEDs lie just beneath. In this latter case the recesses may be closed by use of a transparent or translucent covering layer (for example, being waterproof and/or sacrificial, as discussed previously). In either case, when lit to a least above a threshold brightness, the LEDs are visible when viewing the upper surface of the exercise mat.

It will be understood that the upper surface of the exercise mat is that which the user of the mat exercises on, whilst the lower surface rests upon some underlying support such as a floor. Subsequent references to a surface of the mat herein refer to the upper surface of the exercise mat unless otherwise stated.

The exercise mat may comprise a plurality of lights (A, B, C) distributed over its upper surface, or these may be restricted to at or near the long edges (A, C) or even just one long edge (A or C) of the surface.

Figure 3:
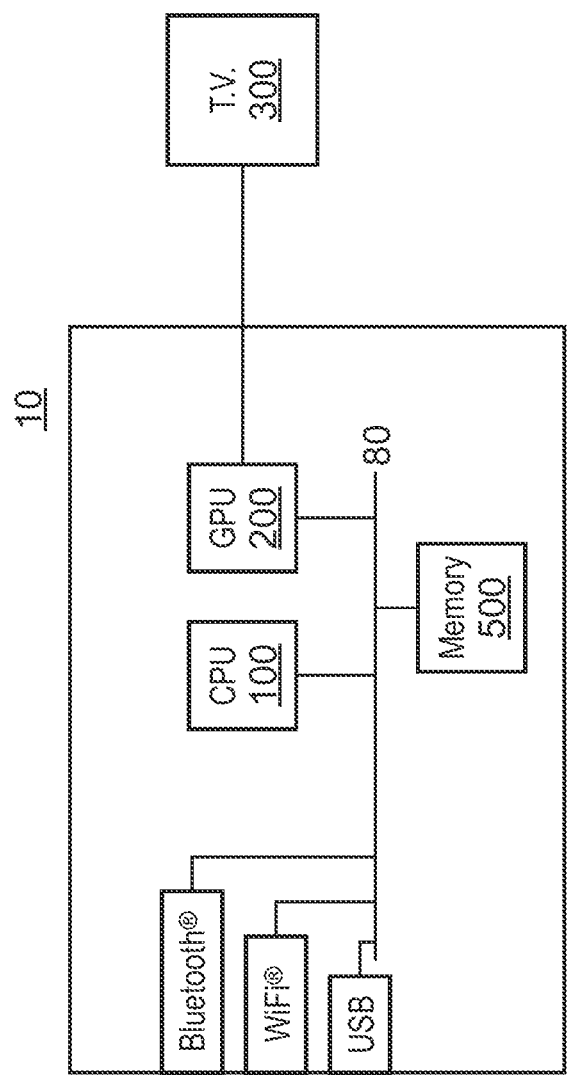
FIG. 3 is a schematic diagram of an entertainment device in accordance with an embodiment of the present invention.

In each case, the lights form a predetermined pattern on the upper surface. Referring briefly to FIG. 3, an entertainment device (10), such as a Sony PlayStation 4®, operably coupled to a video camera (756) via a video input means such as USB (710), Bluetooth® (740) or Wifi® (730), is arranged under suitable software instruction to receive captured video images from the video camera and detect some all of the lights on the upper surface of the mat, and correlate these with the predetermined pattern to determine the position and orientation of the mat within the captured video image. The lights themselves and hence their positions can be detected within the captured video image based upon their characteristic brightness and small size.

In an embodiment of the present invention, the lights are distributed in a pattern having some asymmetric properties, in terms of the pattern changing between different parts of the mat, and/or in terms of the density of lights per unit area and/or the colour of lights. Differences in the pattern or pattern density or colour may be partially or wholly abstract and/or may relate to user activities, such as lights or additional lights or colours in regions corresponding to common hand, feet and head positions for the user during exercise. This asymmetry assists with disambiguation of the orientation of the mat when only one orientation of the mat will result in proper correlation with the predetermined asymmetric pattern.

Optionally, and particularly in a case where the lights are restricted to just one long edge of the mat, then either a known colour of the mat or the colour detected between lights of the mat (i.e. the actual colour of the mat as detected by the video camera under current lighting conditions) can be used to determine the block region of the image corresponding to the mat. In this way, disambiguation is achieved by determining the orientation of the long edge of the mat, together with colour information indicating to which side of the lights the remainder of the mat is located.

Referring now also to FIGS. 2A-E, in addition to determining the position and orientation of the mat, the lights and optionally the shape of the block region of colour corresponding to the mat within the captured video image can be used to indicate a configuration of shape adopted by the exercise mat due to the surface it is resting upon.

Figure 2A:
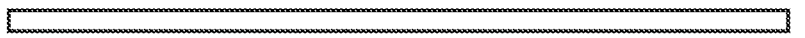
FIGS. 2A-E are schematic diagrams of an exercise mat each showing a different configuration of shape for the mat due to the surface upon which it is lying, as in accordance with an embodiment of the present invention.

FIG. 2A shows a side-on view of the mat when lying on a flat and hard surface. As such it may be thought of as a default configuration of shape for the mat in use, and the pattern of lights that will be visible to the video camera and hence also the entertainment device may also be thought of as the default configuration for the pattern of lights, and will indicate a flat shape for the mat.

For clarity, each of FIGS. 2B-E also show a side on-view of the mat adopting different shapes, and hence do not illustrate the pattern of lights on the upper surface of the mat. However it will be appreciated that for different configurations of shape of the mat, the configuration of the pattern of lights visible to the video camera and hence the entertainment device will be distorted in a corresponding fashion. As will be described below, the entertainment device is then operable to detect the distortion and hence the corresponding shape of the mat.

Figure 2B:
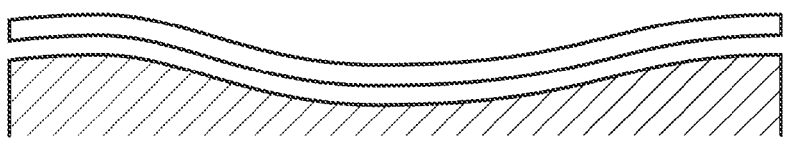

FIG. 2B illustrates the exercise mat being placed on a flat but soft surface such as a bed. In such circumstances, the mat will form a shallow concave shape when the user is on it, and this will be indicated by a relative curvature of the pattern of remaining visible lights with respect to the default configuration.

Upon detecting such relative curvature characteristic of the mat being placed on a flat but soft surface, the entertainment device may for example restrict the range of exercises in an exercise program to avoid exercises that are unsafe or potentially injurious when conducted on a soft surface instead of a hard surface, and/or conversely enable exercises better suited to a soft surface.

Figure 2C:
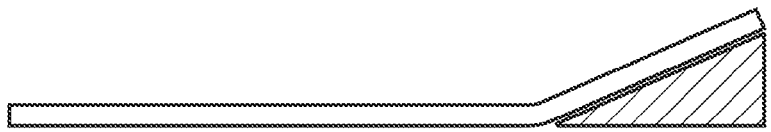
Figure 2D:
Figure 2E:
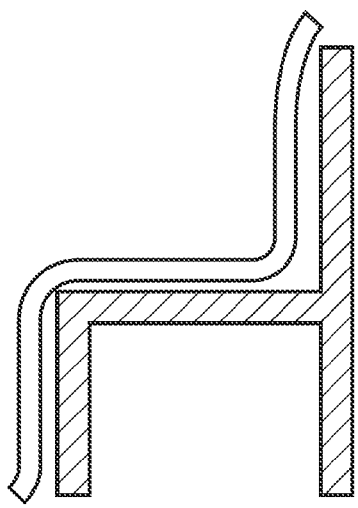

FIGS. 2C-E illustrate the exercise mat being used in conjunction with other equipment, illustrated using hatching in the figures. As will be explained below, in an embodiment of the present invention the entertainment device may comprise templates for different configurations of the pattern of lights corresponding to each such piece of equipment whose use with the mat is supported in an application running on the entertainment device, and/or may comprise means to estimate the configuration according to the relative angle or angles between portions of the mat.

FIG. 2C illustrates the exercise mat raised at one end by a wedge pillow. In such circumstances, the mat will adopt a configuration of two flat parts having a relative angle to each other that is less than 180°, for example by a threshold amount. Put another way, the mat will adopt a configuration in which a portion of the mat has an incline that is more than a threshold amount relative to a portion that is in the default configuration. The threshold in either case can be used for example to distinguish between the mat resting on a wedge pillow and merely crossing the edge of a rug.

The change in configuration will result in a corresponding change to the configuration of the pattern of lights detectable by entertainment device. It will also be appreciated that the block region of colour in the image corresponding to the mat will correspondingly change shape. The entertainment device is operable to detect such a modified configuration, either with reference to a template comprising a modified version of the light pattern incorporating such an incline (and optionally a template modelling the shape of the block region of colour corresponding to the mat), or by detecting the part of the mat having the default configuration and hence default configuration of lights, and then evaluating the remaining part of the mat with respect to the remainder of the of the default configuration by rotating that pattern by successive angles until a close match is detected. In this latter technique, it will be appreciated that in effect a 3D model of the pattern is oriented in a manner indicated by the part of the light pattern corresponding to the default configuration, and then that part of the model of the light pattern that does not appear to correspond to the default configuration is rotated or bent upwards with respect that orientation at successive angular increments until a best match with the observed light pattern in the captured video image is found.

Upon detecting such a relative angle or equivalently such a relative incline, the entertainment device again may deselect or select exercises or game activities appropriate to the configuration of the mat.

FIG. 2D similarly shows the mat placed over a step, such as a step-aerobic step. Again this results in a change to the configuration of the mat and a corresponding change to the configuration of the pattern of lights, this time in a step-like a configuration rather than an inclined configuration.

Again, the entertainment device may comprise a template having a predetermined variant of the default pattern for the case where the mat is in a step-like configuration, or alternatively the entertainment device may detect the part of the mat that is in the default configuration, and then, as in the case for FIG. 2C, detect the relative incline for the next part of the mat, and here where the incline is greater than the threshold angle (as a non-limiting example, greater than 70°), assume that the mat is in a step configuration, and then also search for an upper flat portion of the mat that is roughly parallel with the portion of the mat in the default configuration.

In either case once the configuration of the mat has been detected, again the entertainment device may disable or enable exercises or game functionality relating to the configuration of the mat; hence for example exercises such as sit-ups may be disabled or a different version of these may be presented that makes use of the step, whilst step exercises may be added to an exercise regime.

Finally FIG. 2E shows the mat in a seating configuration, in which only the central portion of the mat is substantially in the default configuration whilst each end is substantially vertical. Again the entertainment device may have a template comprising a predetermined variant configuration for the pattern of lights that corresponds to this usage, or may detect the relative inclines of different portions of the mat as explained previously.

In this case, if this configuration of the mat has been detected, then the entertainment device may deselect or select activities suited to this configuration. For example the entertainment device may add sitting and standing exercises, or where the mat comprises pressure sensors, the entertainment device may be used to monitor the posture of the user over a long period of time (for example when the user is playing a videogame, or watching a movie).

In an embodiment of the present invention, in a first mode then as described above the lights in the mat provide means by which the entertainment device can determine the configuration of shape of the mat due to the surface upon which it is then placed.

However optionally the mat may then operate in other modes, as described below.

To provide an interactive experience, optionally the mat (1) comprises a lighting control input adapted to receive signals from the remote entertainment device (10). The input may be a wired input (not shown) physically connecting the mat to the entertainment device or a further peripheral device that is also in communication with it; this wired input may also provide power to the mat's lights. Alternatively where the mat has an independent power source such as batteries or an external power supply (not shown), the input may be a wireless input (not shown) based on a communication standard such as Bluetooth®.

The signals received from the entertainment device may control one or more selected from the list consisting of:
  i. The activation or deactivation of the plurality of lights;
  ii. the activation or deactivation of a subset of the plurality of lights;
  iii. a brightness level of some or all of the lights; and
  iv. a colour of some or all of the lights.

In this way, entertainment device can for example indicate target positions for the user on the mat by selective activation or deactivation of one or more lights, or making one or more lights brighter or change colour as appropriate. Similarly the entertainment device can for example pulse or otherwise modify the activation, brightness or colour of one or more of the lights in response to a soundtrack or rhythm associated with the exercise or game activity, so that the user has visual guidance even when they are in a position that makes looking at a television (300) associated with the entertainment device difficult.

Hence for example if the user is doing push-ups and has two face towards the mat, one or more lights roughly opposite the user's face can activate, change brightness and/or change colour in response to a preferred rate of push-ups.

Similarly, in a second mode, the entertainment device may activate, change brightness and/or change the colour of lights on the mat in response to the detected configuration of shape of the mat. For example with reference to FIG. 2C, the lights on the portion of the mat inclined by the wedge may be made dimmer or use a different colour to the lights on the flat, default portion of the mat. Alternatively or in addition exercise specific changes to the lights that correspond to exercises relevant to that configuration of the shape of the mat may be used; for example a region on the inclined portion of the mat may be illuminated that corresponds to a position for the user to place their head.

Alternatively or in addition to receiving control signals from the entertainment device, in an embodiment of the present invention the exercise mat may transmit signals to the entertainment device, again either via a wired or wireless connection. In this case, the exercise mat may comprise one or more pressure sensors incorporated into the flexible body of the mat, and the mat transmits signals indicative of pressure values from the or each pressure sensor to the entertainment device.

This allows the entertainment device to determine the amount of pressure exerted by the user on the pressure sensors. Where a sufficient number of pressure sensors are evenly distributed within the mat, entertainment device can estimate the weight distribution of the user and the approximate position of the user on the mat. Where pressure sensors are only located at key points, such as for example expected positions for hands, feet and/or head for certain exercises, then the entertainment device can detect whether the user is placing their hands, feet or head as applicable at the right position during the exercise.

In addition, it will be appreciated that the entertainment device may detect which lights in the known pattern of lights on the mat are being occluded by the user, and this information in conjunction with the known position and orientation of the mat within the captured video image may also be used to estimate the position of the user.

Alternatively or in addition, the entertainment device may analyse the captured video image to detect the user directly; information regarding the position and orientation of the mat and the expected posture of the user can be used to correlate an image of the user with a skeletal model or similar template version of the user and determine how well the user is performing an exercise.

Optionally the user may hold or wear further illuminated markers for certain exercises, for example those which primarily involve standing on the mat and doing upper body exercises. The illuminated markers may for example be one or more PlayStation Move® controllers.

Again to provide feedback to the user, in a third mode, the activation, brightness and/or colour of a subset of the plurality of lights can be responsive to their proximity to a pressure sensor incorporated into the flexible body of the exercise mat.

In an embodiment of the present invention these changes to the lights are controlled by the entertainment device as described previously and are responsive to the exercise or game application. Hence for example if the user is asked to do star jumps, lights on or surrounding pressure points where it is desired for the user to land may be illuminated by the entertainment device.

Alternatively or in addition, the mat may optionally have a stand-alone mode where it does not require control by the entertainment device; in these circumstances the lights on the mat will not change in response to the configuration of shape of the mat as there is no separate detection mechanism, but the lights may be coupled to pressure sensors in the mat so that when the user places their hand, foot or head at a position on the mat that is equipped with a pressure sensor, lights on or surrounding that sensor illuminate, change brightness or change colour.

In addition to the lights and optionally the pressure sensors, additional feedback may be incorporated into the mat by use of vibration units incorporated into the flexible body of the exercise mat. The vibration units are typically electric motors with a weight distribution that is not axially balanced, such as those found in mobile phones and the like. Again in an optional stand-alone mode, these vibration units may vibrate for example to prompt the user to lift their hand or foot in time to a rhythm. Meanwhile when in communication with the remote entertainment device, a vibration control input (which may share the same wired or wireless to communication means as other inputs or outputs mentioned herein) receives signals controlling the or each vibration unit within the mat responsive to the exercise or game application.

Accordingly in a fourth mode, the activation, brightness and/or colour of a subset of the lights may be made responsive to the location and activation of a vibration unit. Again in an optional stand-alone mode, this may take the form of lights near to a vibration unit activating, changing brightness and/or colour when the vibration unit is activated; this helps the user know that the vibration unit has been activated if their hand is not in the correct position to feel it. Meanwhile when in communication with the entertainment device, the lights may similarly change when the vibration unit activates, but do so under the control of the entertainment device. In this case however the entertainment device can also use the lights in advance of the vibration unit activating, for example to create a game where a user must lift their hand, foot or head as applicable off the mat before the vibration unit activates, based upon a warning light activation, or change in brightness or colour. The user's lifting and return of limbs may be detected as described above by the use of pressure sensors or analysis of the captured video image. The aim of such a game is thus to avoid getting 'buzzed' by vibrations in the mat. An equivalent game can use changes in lighting of the kind described previously. Such games provide exercise without resorting to repetitive exercise activities, and hence may be more attractive to younger users of the mat. Other games relating to chasing lights on the mat, such as a 'hopscotch' type game or a game in which the user has to put their hands and feet on the mat in a predetermined order where indicated by the lights, can also be envisaged.

Optionally, the pattern of lights on the exercise mat may be used to indicate proper placement of the mat into one or more of the above configurations of shape; for example a subset of lights may be positioned on a line defining the point where the mat should be preferably bent by a wedge; in a case where the lights on the mat are controlled by the entertainment device, then these lights may be activated, change brightness and/or change colour to emphasise this line. This has the further advantage of improving the predictability of the modified configuration of shape of the mat, potentially simplifying recognition of the configuration of shape by the entertainment device, for example when evaluated with reference to a template.

It will be appreciated that the mat may have a large number of lights distributed across the surface and hence may be able to define multiple lines in this manner for use in different exercises; hence alternatively or in addition to the line defining the start of an incline as per FIG. 2C, the mat may be able to define lines identifying the fold points for one or more of the configurations shown in FIGS. 2D and 2E. It will be appreciated that the mat does not need to be rectangular as shown in the figures; consequently for other shapes of mat, other changes configuration of shape may be applicable, optionally together the ability to provide corresponding illuminated fold lines.

It will also be appreciated that whilst the pattern of lights on the mat is preferably asymmetrical to allow an unambiguous estimate of position and orientation, this asymmetry may be controlled by the entertainment device. That is to say, the physical distribution of lights on the upper surface of the mat may be uniform, in the sense of being either in a regular pattern or having an even density of distribution across the area of the mat that they occupy. However, in this case when the entertainment device attempts to detect the position and orientation of the mat, it may selectively activate or deactivate lights, and/or change colour of lights (if at least some of the lights are capable of changing colour) to create an asymmetric pattern on the mat for the purposes of detecting its position and orientation. The asymmetric pattern may be static for a period of time, or may comprise a time varying sequence, with one or more lights on the mat being illuminated in sequence (either successively or cumulatively), or a predetermined series of patterns being used.

Hence the asymmetric pattern does not need to be physically embedded within the mat, but can be a software controlled pattern imposed on an otherwise regular and potentially symmetrical physical pattern of lights embedded in the mat. Consequently, at least in the first mode, the exercise mat is operable to change the activation, brightness and/or colour of a subset of the plurality of lights responsive to a lighting control signal defining an asymmetric pattern on the exercise mat.

In an embodiment of the present invention, the mat comprises one or more sensors suitable for detecting the bending or flexure of the mat, such as one or more strain gauges. The or each flexure sensing unit may be placed randomly, or in an even distribution, or at key positions on the mat, such as for example at points of flexure that may correspond to printed lines or other indicators on the mat that in turn encourage the user to position the mat so as to bend at those indicators, for example to form the configurations illustrated in FIGS. 2C, 2D or 2E.

The mat may then transmit output readings from the sensors to the entertainment device, which may monitor such sensors for example to protect the mat (and in particular its internal electronics) from damage; if the mat is being bent too much, entertainment device may issue a visible or audible alert on a screen and/or illuminate some or all of the lights in the mat in red, for example.

The entertainment device may similarly monitor the sensors to warn the user against potentially unhealthy actions; taking the example of FIG. 2B, if the mat is placed on too soft a surface, the resulting deformation of the mat underneath the user may be detected using the sensors, thereby causing the entertainment device either to warn the user that certain exercises may risk injury, and/or to skip or shorten such exercises if they occur within a sequence of exercises.

It will be appreciated that damage detection for the mat and/or the user may similarly be implemented in an optional stand-alone mode of the mat, if provided.

Such a bending/flexure sensor may also be used for intentional input by the user; for example, a gauge may be put in/near one or more corners of the mat, so that the user can generate an input signal by flicking up the corner of the mat with a hand or a toe/heel; this may be the most suitable and ergonomic means for the user to interact with the system when they are in certain positions on the mat. In this case, the detected flexure of the corner of the mat will be interpreted by the entertainment device as similar to a button press, with the meaning of the flicking action either being fixed (e.g. 'pause'), or being context sensitive depending on the state of the application. Hence more generally, the entertainment device is operable to detect an input from the user responsive to a flexure value from a flexure sensor located at a predetermined position in the exercise mat.

Turning now also to FIG. 3, the entertainment device itself (10) is typically a video games console such as the Sony PlayStation 4®, but may equally be a portable games device such as the PlayStation Vita®, or a tablet or smartphone device, laptop, PC, set-top box, smart television or other suitable device capable of exerting wired or wireless control over the exercise mat and capable of receiving a captured video image of a scene comprising said flexible exercise mat having a plurality of lights visible on the surface. Input means for receiving the captured video image may be for an external video camera (and may be wired or wireless as discussed previously) or may be for a built-in video camera, depending on the device.

The entertainment device comprises image processing means such as for example a central processing unit (100) optionally operating in conjunction with a graphics processing unit (200) to detect the positions of the visible plurality of lights within the video image. The CPU and GPU typically communicate with each other and respective inputs and outputs via a common bus (80). The CPU and optionally the GPU run software instructions stored in memory (500), which may collectively refer to read-only memory, random access memory, hard drive and/or any other electronic, magnetic or optical storage medium.

The entertainment device also comprises processing means such as again the central processing unit, acting under suitable software instructions, to calculate a configuration of shape adopted by the exercise mat based upon the detected positions of the plurality of lights. As noted above this may be achieved by correlating a known pattern of the lights with the detected positions of lights within the video image, to determine a position and orientation for at least a part of the mat, and either making reference to predefined templates for different configurations of shape of the mat, or detecting one or more angles of bend of the mat to detect inclines or step-like configurations of shape of the mat.

The entertainment device is then operable under suitable software instructions to modify a behaviour of an application run by the entertainment device in response to a shape of the exercise mat calculated by the processing means. In practice, this may take the form of the application modifying its own behaviour. Hence as described above the application may deselect or select exercise or game activities in response to the detected shape of the exercise mat, and/or change the activation, brightness and/or colour of some or all of the lights on the mat in response to the detected shape of the exercise mat.

As noted previously, in an embodiment of the present invention the entertainment device can control feedback features built into the mat such as the lighting and optionally vibration units. With regard to the lighting, a wired or wireless connection on the entertainment device such as a USB port (710) or a Bluetooth® (740) or Wi-Fi® link (730) may act as control output means adapted to transmit, to a remote exercise mat comprising a plurality of lights, signals controlling one or more selected from the list consisting of:
 i. The activation or deactivation of the plurality of lights;
 ii. the activation or deactivation of a subset of the plurality of lights;
 iii. a brightness level of some or all of the lights; and
 iv. a colour of some or all of the lights.

Consequently, and again as noted previously, the entertainment device can therefore modify the activation, brightness and/or colour of a subset of the plurality of lights to indicate a target position on the exercise mat for a user. Again as described previously, a target position may relate to the position of a pressure pad or a vibration unit, or may relate to a starting position for an exercise or any further position during an exercise at which to place a hand, foot or head as applicable, or during a game may represent an area that a user needs to touch, for example within a predetermined period of time, or an area that a user needs to avoid, again for example within a predetermined period of time.

With regard to the vibration units, as noted previously entertainment device can similarly selectively control activation and deactivation of these units and potentially also a degree vibration depending on the units provided in the mat.

Again as described previously, in an embodiment of the present invention the entertainment device, operating under suitable software instruction, is adapted to estimate a pose of a user of the flexible mat responsive to which of the plurality of lights is visible within the captured video image. Given that the pattern of lights is known, and the position and orientation of the exercise mat is derivable from the pattern of lights within the captured video image, then once the user occupies the mat the entertainment device can estimate the user's current pose, based upon which lights are occluded by the user. Hence for example the entertainment device can detect whether the user is standing upright, sitting down or lying down depending on which lights are occluded given the current position and orientation of the mat with respect to the video camera. This may enable the entertainment device for example to detect that the user is ready to begin a new exercise that has an initial position either standing, sitting or lying down, as applicable. This is particularly useful in a case where the mat either has no pressure sensors or does not directly communicate with the entertainment device via a wired or wireless link.

It will be appreciated that the entertainment device as described herein and the exercise mat as described herein, optionally in conjunction with an external video camera, together form a system for interactive use of an exercise mat. It will also be appreciated that more than one exercise mat may be associated with the entertainment device to create a multiplayer system, in which the configuration of shape of each exercise mat is determined from a captured video image showing the or each mat. Similarly the above-described communications between the entertainment device and a first mat can be replicated for additional mats.

It will be appreciated that multiplayer exercises and games may therefore be provided for users on respective mats. Similarly for a single mat, for example placed across a sofa, a plurality of users could play a game such as musical chairs, where the mat detects the last person to sit when music is paused, or indicates with its lights one or (under instruction from the entertainment device) more specific regions of the mat to touch when the music is paused.

Figure 4:
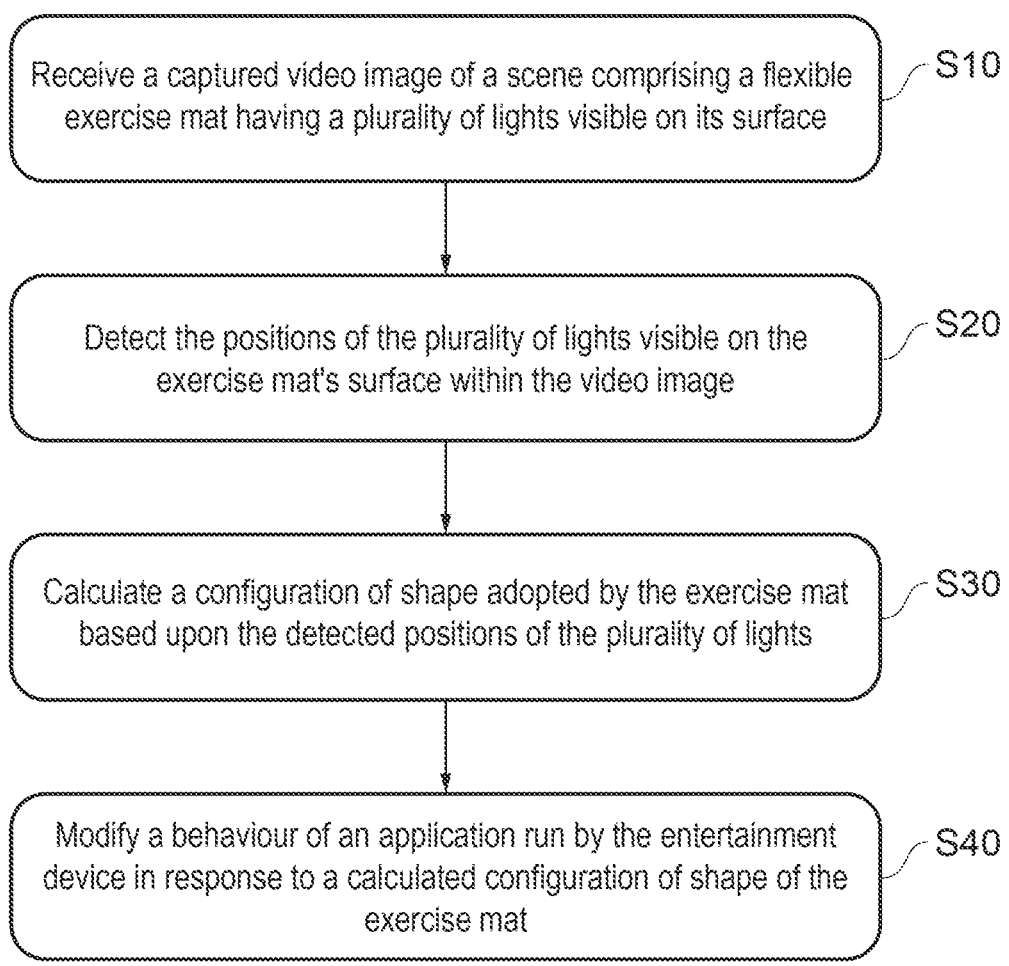
FIG. 4 is a flow diagram of a method of interaction between an entertainment device and exercise mat in accordance with an embodiment of the present invention.

Turning now to FIG. 4, a method of interaction between an entertainment device and an exercise mat comprises:
 in a first step s10, receiving a captured video image of a scene comprising a flexible exercise mat having a plurality of lights visible on its surface;
 in a second step s20, detecting the positions of the plurality of lights visible on the exercise mat's surface within the video image;
 in a third step s30, calculating a configuration of shape adopted by the exercise mat based upon the detected positions of the plurality of lights; and
 in a fourth step s40 modifying a behaviour of an application run by the entertainment device in response to a calculated configuration of shape of the exercise mat.

The method may be used once for an initial calibration of the mat's configuration of shape, or may loop continuously or periodically to re-establish the position and orientation of the mat (for example to determine whether the mat has moved due to sipping on the floor) or any change to the configuration of shape due to repositioning of the mat by the user Similarly the method may be triggered by user inputs to the application running on the entertainment device, such as the selection of an exercise relevant to a particular configuration of shape of the mat that is different to the one previously calculated in the third step above.

As described previously this method may further comprise a step of modifying the activation, brightness and/or colour of a subset of the plurality of lights to indicate a target position on the exercise mat for a user.

Similarly, as described previously this method may further comprise steps of detecting which of the plurality of lights is visible within the captured video image, and estimating a pose of a user of the flexible mat responsive to which of the plurality of light of visible within the captured video image.

Further steps may be considered in conjunction with the method described above, such as transmitting and receiving pressure sensor data, transmitting and receiving vibration unit control data, and transmitting lighting control data to generate an asymmetric lighting pattern for the purposes of detecting the position and orientation of the mat within captured video images.

Again as described previously, the method may also comprise subsequently estimating a pose of the user based upon which lights are occluded within the captured video image.

It will be appreciated more generally that the method of interaction between an entertainment device and an exercise mat may be implemented by suitable software instructions run on entertainment device as described previously.

It will be appreciated that the above methods may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a tangible non-transitory machine-readable medium such as a floppy disk, optical disk, hard disk, PROM, RAM, flash memory or any combination of these or other storage media, or realised in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these of other networks.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An exercise system, comprising:
   a flexible exercise mat, comprising:
      a flexible body; and
      a plurality of lights incorporated into the flexible body and visible in use on a surface of the flexible body; and
   an entertainment device, comprising:
      an input configured to receive a captured video image of a scene comprising the flexible exercise mat having the plurality of lights visible on its surface;
      an image processing device configured to detect the positions of the plurality of lights within the video image; and
      a processing device configured to calculate a configuration of shape adopted by the exercise mat based upon the detected positions of the plurality of lights;
   wherein:
      in a first mode, the plurality of lights are arranged to indicate a configuration of shape adopted by the exercise mat due to a surface upon which it has been placed, and
      the entertainment device is configured to modify a behaviour of an application run by the entertainment device in response to a configuration of shape of the exercise mat calculated by the processing device.

2. An exercise system according to claim 1, in which the mat further comprises:
   a lighting control input configured to receive, from a remote entertainment device, signals controlling one or more selected from the list consisting of:
   i. activation or deactivation of the plurality of lights;
   ii. the activation or deactivation of a subset of the plurality of lights;
   iii. a brightness level of some or all of the plurality of lights; and
   iv. a colour of some or all of the plurality of lights.

3. An exercise system according to claim 1 in which, in a second mode, an activation, a brightness, and/or a colour of a subset of the plurality of lights is responsive to the configuration of shape adopted by the exercise mat due to the surface upon which it has been placed.

4. An exercise system according to claim 1, in which the flexible exercise mat further comprises:
   one or more pressure sensors incorporated into the flexible body of the flexible exercise mat; and
   a pressure level output configured to transmit, to a remote entertainment device, signals indicative of pressure values from at least one of the one or more pressure sensors.

5. An exercise system according to claim 1 in which, in a second mode, an activation, a brightness, and/or a colour of a subset of the plurality of lights is responsive to a proximity of the subset to a pressure sensor incorporated into the flexible body of the exercise mat.

6. An exercise system according to claim 1, in which the flexible exercise mat further comprises:
   one or more vibration units incorporated into the flexible body of the flexible exercise mat, and
   a vibration control input configured to receive, from a remote entertainment device, signals controlling at least one of the one or more vibration units.

7. An exercise system according to claim 1, in which the flexible exercise mat further comprises:
   one or more flexure sensing units incorporated into the flexible body of the flexible exercise mat; and
   a flexure level output configured to transmit, to a remote entertainment device, signals indicative of flexure values from at least one of the one or more flexure sensors.

8. An exercise system according to claim 2 in which, in the first mode, the flexible exercise mat is configured to change the activation, brightness level, and/or colour of a subset of the plurality of lights responsive to a lighting control signal defining an asymmetric pattern on the flexible exercise mat.

9. An exercise system according to claim 1, in which the entertainment device further comprises a lighting control output to transmit, to the flexible exercise mat, signals controlling one or more selected from the list consisting of:
  i. activation or deactivation of the plurality of lights;
  ii. the activation or deactivation of a subset of the plurality of lights;
  iii. a brightness level of some or all of the plurality of lights; and
  iv. a colour of some or all of the plurality of lights.

10. An exercise system according to claim 9, in which the entertainment device is configured to modify the activation, brightness level, and/or colour of the subset of the plurality of lights to produce an asymmetric pattern on the flexible exercise mat.

11. An exercise system according to claim 1, in which the entertainment device is configured to estimate a pose of a user of the flexible exercise mat responsive to which of the plurality of lights is visible within the captured video image.

12. An exercise system according to claim 1, in which the entertainment device is configured to detect an input from a user responsive to a flexure value from a flexure sensor at a predetermined position in the flexible exercise mat.

* * * * *